US010357189B2

(12) United States Patent
Koide et al.

(10) Patent No.: US 10,357,189 B2
(45) Date of Patent: Jul. 23, 2019

(54) BIOLOGICAL INFORMATION ACQUISITION DEVICE AND BIOLOGICAL INFORMATION ACQUISITION METHOD

(71) Applicant: Seiko Epson Corporation, Tokyo (JP)

(72) Inventors: Yasunori Koide, Matsumoto (JP); Tetsuji Fujita, Chino (JP); Takashi Toya, Chino (JP)

(73) Assignee: Seiko Epson Corporation (JP)

( * ) Notice: Subject to any disclaimer, the term of this patent is extended or adjusted under 35 U.S.C. 154(b) by 213 days.

(21) Appl. No.: 15/422,768

(22) Filed: Feb. 2, 2017

(65) Prior Publication Data
US 2017/0215778 A1 Aug. 3, 2017

(30) Foreign Application Priority Data

Feb. 3, 2016 (JP) .................................. 2016-018549

(51) Int. Cl.
A61B 5/00 (2006.01)
A61B 5/145 (2006.01)
A61B 5/1455 (2006.01)

(52) U.S. Cl.
CPC ........ A61B 5/14552 (2013.01); A61B 5/1455 (2013.01); A61B 5/14532 (2013.01);
(Continued)

(58) Field of Classification Search
CPC ... A61B 5/14552; A61B 5/489; A61B 5/1455; A61B 5/681; A61B 5/14532;
(Continued)

(56) References Cited

U.S. PATENT DOCUMENTS

2007/0085995 A1* 4/2007 Pesach ............... A61B 5/14532
356/39
2010/0331640 A1* 12/2010 Medina ............. A61B 5/14535
600/324

(Continued)

FOREIGN PATENT DOCUMENTS

JP 2014-124453 A 7/2014
JP 2014-124455 A 7/2014
(Continued)

Primary Examiner — Eric F Winakur
Assistant Examiner — Abid A Mustansir
(74) Attorney, Agent, or Firm — Harness, Dickey & Pierce, P.L.C.

(57) ABSTRACT

A biological information acquisition device includes: a light emitting unit which casts light on a living body; a plurality of light receiving units which receives the light transmitted through the living body; and a control unit which controls the light emitting unit and the light receiving units. The control unit causes the light emitting unit to emit light as a measurement light emitting unit, causes a plurality of measurement light receiving units spaced apart from the measurement light emitting unit by a first distance, of the plurality of light receiving units, to receive the light cast from measurement light emitting unit and thus acquires a plurality of light receiving results, and acquires biological information using a first light receiving result with a highest light reception intensity and a second light receiving result with a lowest light reception intensity, of the plurality of light receiving results.

8 Claims, 10 Drawing Sheets

(52) U.S. Cl.
CPC .............. *A61B 5/489* (2013.01); *A61B 5/681* (2013.01); *A61B 2560/0475* (2013.01); *A61B 2562/0238* (2013.01); *A61B 2562/046* (2013.01)

(58) Field of Classification Search
CPC ...... A61B 2562/0238; A61B 2562/046; A61B 2560/0475
See application file for complete search history.

(56) References Cited

U.S. PATENT DOCUMENTS

| | | |
|---|---|---|
| 2015/0182150 A1 | 7/2015 | Ikeda |
| 2015/0216454 A1 | 8/2015 | Kasahara et al. |

FOREIGN PATENT DOCUMENTS

| | | |
|---|---|---|
| JP | 2015-123341 A | 7/2015 |
| JP | 2015-142666 A | 8/2015 |

\* cited by examiner

BIOLOGICAL INFORMATION ACQUISITION DEVICE AND BIOLOGICAL INFORMATION ACQUISITION METHOD

BACKGROUND

1. Technical Field

The present invention relates to a biological information acquisition device and a biological information acquisition method.

2. Related Art

According to the related art, a biological information acquisition device which acquires biological information about blood vessels and blood in blood vessels is known (for example, JP-A-2015-142666). JP-A-2015-142666 discloses that biological information is acquired using (i) a light receiving result acquired by alight receiving element located at a measurement light receiving position and (ii) a light receiving result acquired by a reference light receiving element located at a reference light receiving position, with respect to light cast from a light emitting element located at an irradiation position.

JP-A-2015-142666 and JP-A-2014-124455 disclose the following about the positional relation between the irradiation position, the measurement light receiving position, and the reference light receiving position. That is, it is described that (i) a blood vessel site which is a measurement target is located at a center part between the irradiation position and the measurement light receiving position and that (ii) the blood vessel site of the measurement target is not located between the irradiation position and the reference light receiving position. Also, JP-A-2015-142666 includes the description about the positional relation between the irradiation position, the measurement light receiving position, and the reference light receiving position that the reference light receiving position is located at a position on an extension line connecting the irradiation position and the measurement light receiving position and opposite to the measurement light receiving position as viewed from the from the irradiation position.

However, in the techniques disclosed in JP-A-2015-142666 and JP-A-2014-124455, since the measurement light receiving position and the reference light receiving position are predetermined before the light emission by the measurement light emitting unit, each position may not necessarily be an optimum position for acquiring biological information related to the blood vessel and therefore the biological information related to the blood vessel may not be acquired with sufficiently high accuracy.

SUMMARY

An advantage of some aspects of the invention is to solve at least a part of the problems described above, and the invention can be implemented as the following forms or application examples.

(1) According to a first aspect of the invention, a biological information acquisition device is provided. This biological information acquisition device includes: a light emitting unit which casts light on a living body; a plurality of light receiving units which receives the light transmitted through the living body; and a control unit which controls the light emitting unit and the light receiving units. The control unit causes the light emitting unit to emit light as a measurement light emitting unit, causes a plurality of measurement light receiving units spaced apart from the measurement light emitting unit by a first distance, of the plurality of light receiving units, to receive the light cast from the measurement light emitting unit and thus acquires a plurality of light receiving results, and acquires biological information using a first light receiving result with a highest light reception intensity and a second light receiving result with a lowest light reception intensity, of the plurality of light receiving results.

Since a blood vessel generally absorbs infrared rays more easily than a non-blood vessel part, the luminance of the light transmitted through a blood vessel has lower luminance than that of the light that is not transmitted through the blood vessel. The biological information acquisition device of this configuration acquires biological information, using (i) a first light receiving result which is a light receiving result with the highest light reception intensity and is considered to include little biological information related to the blood vessel of a plurality of light receiving results, and (ii) a second light reception result which is a light receiving result with the lowest light reception intensity and is considered to include a lot of biological information related to the blood vessel. Therefore, the biological information related to the blood vessel can be acquired with high accuracy.

(2) The biological information acquisition device may include a plurality of the light emitting units. The control unit may specify a position of a blood vessel in the living body by causing at least one of the plurality of light emitting units to emit light, and may select a light emitting unit spaced apart from the blood vessel by a second distance, of the plurality of light emitting units, as the measurement light emitting unit.

According to the biological information acquisition device of this configuration, since the light emitting unit suitable for acquiring biological information related to the blood vessel can be selected as the measurement light emitting unit by specifying the position of the blood vessel, the biological information related to the blood vessel can be acquired with high accuracy.

(3) The biological information acquisition device may include a sensor module having a plurality of light emitting elements and a plurality of light receiving elements, each being arrayed regularly, in a light emitting/receiving area. The control unit may select a light emitting area having a predetermined shape and size, as a part of the light emitting/receiving area, and cause a plurality of light emitting elements in the light emitting area to emit light as the measurement light emitting unit.

According to the biological information acquisition device of this configuration, since one light emitting unit is formed by a set of a plurality of smaller light emitting elements, the position of the light emitting unit can be selected on the basis of the pitch of the smaller light emitting elements and therefore the degree of freedom in selecting the light emitting unit is improved. Also, according to the biological information acquisition device of this configuration, sufficient light emission intensity can be achieved, compared with the case where one light emitting unit is formed by one light emitting element. As a result, according to the biological information acquisition device of this configuration, the biological information related to the blood vessel can be acquired with high accuracy.

(4) The biological information acquisition device may include a sensor module having a plurality of light emitting elements and a plurality of light receiving elements, each being arrayed regularly, in a light emitting/receiving area.

The control unit may select a light receiving area having a predetermined shape and size, as a part of the light emitting/receiving area, and cause a plurality of light receiving elements in the light receiving area to receive light as the light receiving unit.

According to the biological information acquisition device of this configuration, since one light receiving unit is formed by a set of a plurality of smaller light receiving elements, the position of the light receiving unit can be selected on the basis of the pitch of the smaller light receiving elements and therefore the degree of freedom in selecting the light receiving unit is improved. Also, according to the biological information acquisition device of this configuration, a sufficient amount of light received can be achieved, compared with the case where one light receiving unit is formed by one light receiving element. As a result, according to the biological information acquisition device of this configuration, the biological information related to the blood vessel can be acquired with high accuracy.

(5) In the biological information acquisition device, the control unit may select the plurality of measurement light receiving units in such a way that light receiving areas of the measurement light receiving units adjacent to each other partly overlap with each other.

According to the biological information acquisition device of this configuration, a plurality of measurement light receiving units can be selected in such a way that the adjacent light receiving areas partly overlap with each other, and the position of each of the plurality of measurement light receiving units can be selected on the basis of the pitch of the light receiving elements. Therefore, the degree of freedom in selecting the light receiving unit is improved. Consequently, according to the biological information acquisition device of this configuration, the biological information related to the blood vessel can be acquired with high accuracy.

(6) In the biological information acquisition device, the biological information may include glucose concentration in the blood of the living body.

According to the biological information acquisition device of this configuration, the glucose concentration in the blood can be acquired.

(7) In the biological information acquisition device, the biological information may include oxygen saturation level in the blood of the living body.

According to the biological information acquisition device of this configuration, the oxygen saturation level in the blood can be acquired.

The invention can also be implemented in various forms other than the above. For example, the invention can be implemented as a biological information acquisition method in which biological information is acquired by a biological information acquisition device including a light emitting unit which casts light on a living body and a plurality of light receiving units which receives the light transmitted through the living body, a computer program which implements this method, a non-transitory storage medium storing this computer program, and the like.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

A1. Device Configuration

Figure 1:
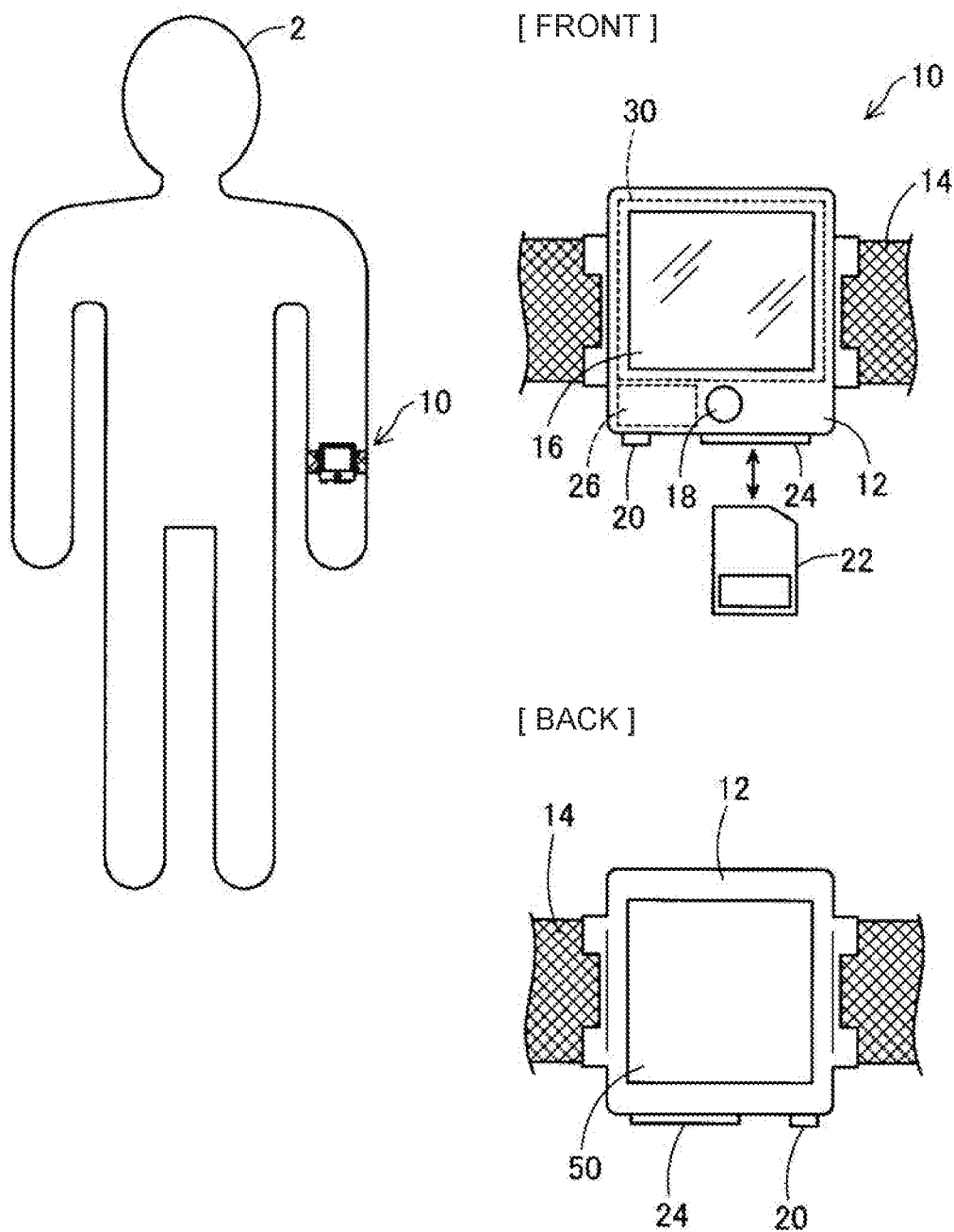
FIG. 1 is a schematic view showing the configuration of a biological information acquisition device according to a first embodiment.

FIG. 1 is a schematic view showing the configuration of a biological information acquisition device 10 according to a first embodiment. The biological information acquisition device 10 is a biological information acquisition device which non-invasively measures biological information of a user 2, using light. In this embodiment, the blood sugar level of the user 2, which is the user's blood glucose concentration, is measured as biological information. The biological information acquisition device 10 is also referred to as a blood sugar level measuring device 10. The biological information acquisition device 10 is a wristwatch-type wearable device including a main body case 12 and a fastening band 14 for mounting and fastening the main body case 12 at a measurement site such as the wrist or arm of the user 2.

On the front side of the main body case 12 (the side facing outward when the device is mounted on the user 2), a touch panel 16 and an operation switch 18 are provided. Using the touch panel 16 and the operation switch 18, the user 2 can input a measurement start instruction or causes the result of measurement to be displayed on the touch panel 16.

On a lateral side of the main body case 12, a communication device 20 for communicating with an external device, and a reader/writer 24 for a memory card 22 are provided. The communication device 20 is realized by an outlet for attaching and detaching a wire cable or by a wireless communication module and antenna for wireless communication. The memory card 22 is a data-rewritable non-volatile memory such as a flash memory, ferroelectric random access memory (FeRAM), or magnetoresistive random access memory (MRAM).

On the back side of the main body case 12, a sensor module 50 is provided in such a way as to be contactable to the skin surface of the user 2. The sensor module 50 is a device for measurement which casts measuring light on the skin surface of the user 2 and receives the light transmitted through or reflected by the body of the user 2, and is a slim image sensor with a built-in light source.

Moreover, the main body case 12 has a rechargeable battery 26 and a control board 30 built inside. As the recharging method for the battery 26, an electrical contact may be provided on the back side of the main body case 12 and the main body case 12 may be set in a cradle connected to a home electricity source so that the battery is recharged via the cradle and the electrical contact, or wireless recharging may be used.

On the control board 30, a CPU (central processing unit), a main memory, a measurement data memory, a touch panel controller, and a sensor module controller are installed. The main memory is a storage medium capable of storing programs and initial setting data and storing computational values by the CPU, and is realized by a RAM, ROM (read only memory), flash memory or the like. The programs and the initial setting data may also be stored in the memory card 22. The measurement data memory is a storage medium for storing measurement data and is realized by a data-rewritable non-volatile memory such as a flash memory, ferroelectric random access memory (FeRAM), or magnetoresistive random access memory (MRAM). The measurement data may also be stored in the memory card 22.

Figure 2:
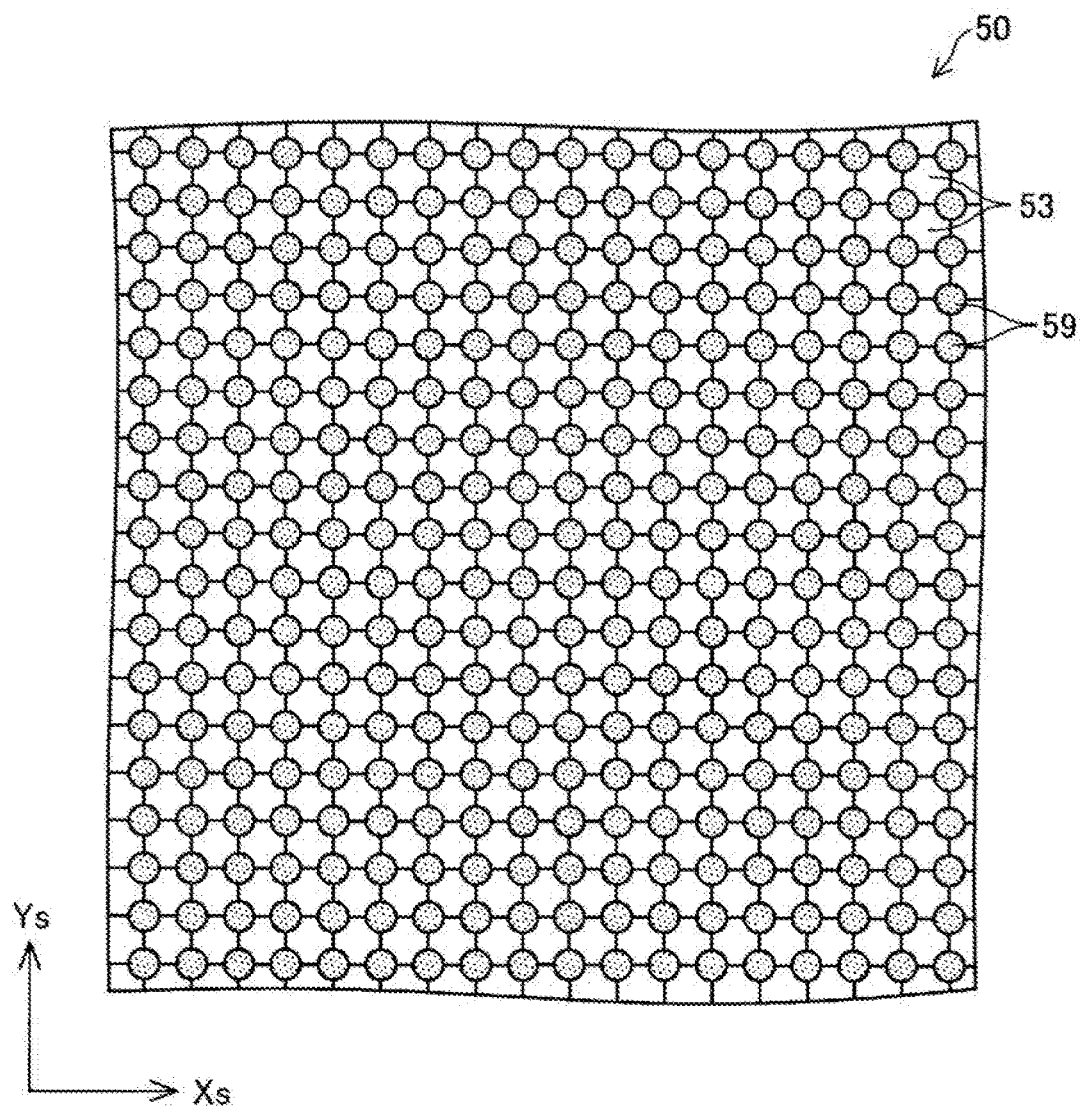
FIG. 2 is a schematic plan view showing a part of a sensor module.
Figure 3:
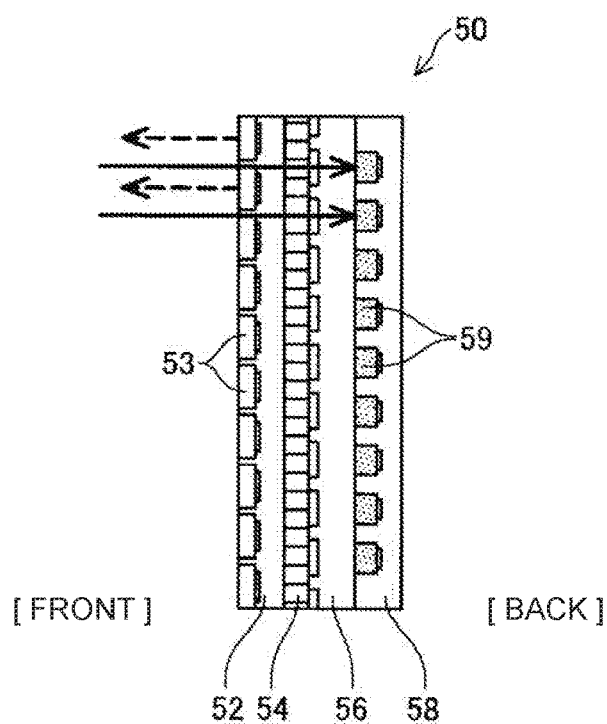
FIG. 3 shows the configuration of the sensor module.

FIG. 2 and FIG. 3 show the configuration of the sensor module 50. FIG. 2 is a schematic plan view showing a part of the sensor module 50. FIG. 3 is a schematic cross-sectional view of the sensor module 50. As shown in FIG. 2, the sensor module 50 has, in its light emitting/receiving area, a plurality of light emitting elements 53 and a plurality of light receiving elements 59, each being arrayed regularly. Here, the light emitting/receiving area refers to an area containing the plurality of light emitting elements 53 and the plurality of light receiving elements 59.

As shown in FIG. 3, the sensor module 50 is an optical sensor formed by stacking a light emitting layer 52 in which multiple light emitting elements 53 are two-dimensionally arrayed on a plane, a light shielding layer 54 which selectively blocks light that is not the light heading toward a light receiving layer 58, a light splitting layer 56 which selectively transmits near-infrared rays, and a light receiving layer 58 in which multiple light receiving elements 59 are two-dimensionally arrayed on a plane. This sensor module 50 is provided on the back side of the main body case 12 in such a way that the front side (the surface on the side of the light emitting layer 52) faces the skin surface of the user 2.

The light emitting element 53 is a site from which light is cast on a living body and is realized by an LED (light emitting diode), OLED (organic light emitting diode) or the like, for example. The light emitting element 53 is an element capable of emitting light including near-infrared rays having a subcutaneous penetration ability in order to measure the blood sugar level (blood glucose concentration) in the embodiment.

The light receiving element 59 is a site where light transmitted through or reflected by a living body is received and from which an electrical signal corresponding to the amount of light received is outputted. The light receiving element 59 is realized by an image pickup element such as a CCD (charge coupled device image sensor) or CMOS (complementary metal oxide semiconductor image sensor). One light receiving element 59 includes a plurality of elements for receiving each wavelength component of light necessary for measuring.

As shown in FIG. 2, the light emitting elements 53 and the light receiving elements 59 are arranged in the form of a matrix defined by a common Xs-Ys orthogonal coordinate system. The light emitting elements 53 and the light receiving elements 59 are arranged with the same spacing in each of the Xs and Ys axis directions but alternately in the Xs-Ys plane. That is, the light emitting elements 53 and the light receiving elements 59 are arranged in such a way that the positions in the Xs and Ys axis directions of the light emitting elements 53 and the light receiving elements 59 are shifted from each other by a predetermined length.

The spacing between the respective light emitting elements 53 and between the respective light receiving elements 59 can be suitably set. For example, the spacing may be preferably 1 to 500 μm. In consideration of the manufacturing cost and the measurement accuracy, the spacing can be 50 to 200 μm, for example. Also, the configuration in which the light emitting elements 53 and the light receiving elements 59 are stacked is not limiting, and the light emitting elements 53 and the light receiving elements 59 may be juxtaposed.

A2. Measurement Principle (A) Measurement of Blood Sugar Level

The blood sugar level measurement principle in this embodiment will be described. In measurement, the biological information acquisition device 10 is fastened with the fastening band 14, with the sensor module 50 in tight contact with the skin surface of the user 2. As the sensor module 50 is in tight contact with the skin surface, factors in lowering the measurement accuracy such as reflection of measurement light on the skin surface and diffusion of measurement light near the skin surface can be restrained. Then, a blood vessel in the living tissue directly below the sensor module 50 is set as a measurement target, and light including transmitted light of the measurement light transmitted through the blood vessel is received to find the light absorption spectrum. Thus, the blood sugar level is estimated and computed.

(A-1) Acquisition of Blood Vessel Pattern

Specifically, a blood vessel pattern (blood vessel position) as viewed from the skin surface is acquired first. The acquisition of the blood vessel pattern can be realized similarly to the vein pattern detection in the known vein authentication technique.

Figure 4:
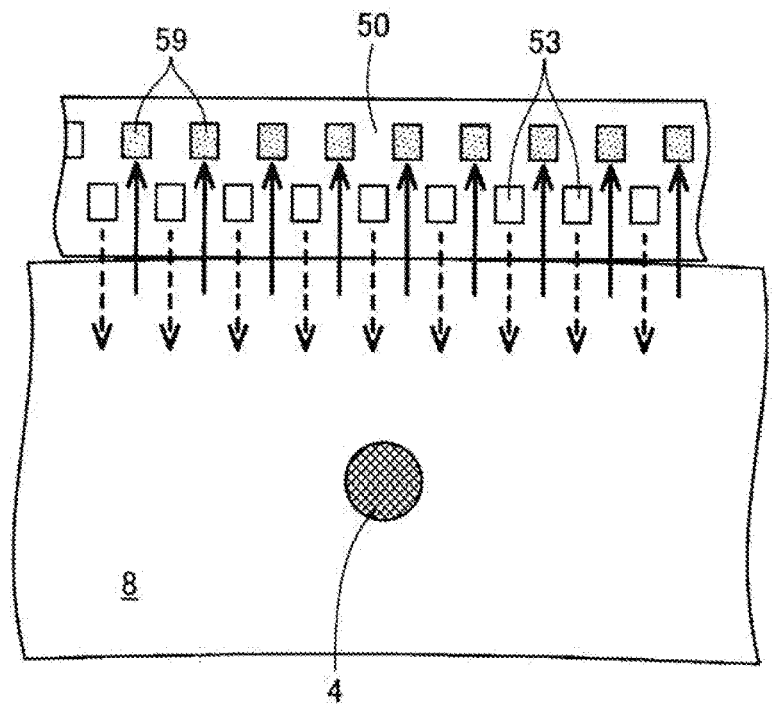
FIG. 4 is a schematic view for explaining the way a blood vessel pattern (blood vessel position) is acquired.

FIG. 4 is a schematic view for explaining the way the blood vessel pattern (blood vessel position) is acquired. As shown in FIG. 4, the light emitting elements 53 of the sensor module 50 is made to emit light at a time and thus cast measurement light on the skin surface of the user 2. Then, using all of the light receiving elements 59, the light (transmitted light) of the measurement light transmitted through the living tissue or the light (reflected light) of the measurement light reflected by the living tissue is received, that is, photographed, to acquire a biological image. In the acquisition of the biological image, it is possible to cause only a part of the light emitting elements 53 of the sensor module 50 to emit light.

The blood vessel absorbs near-infrared rays more easily than non-blood vessel parts. Therefore, in the acquired biological image, the blood vessel part has lower luminance and therefore appears darker than the non-blood vessel parts. Therefore, the blood vessel pattern can be extracted by extracting the part with lower luminance in the biological image. That is, whether the blood vessel exists directly below the corresponding light receiving element 59 or not, that is, the position of the blood vessel, can be acquired on the basis of whether each pixel forming the biological image has luminance equal to or below a predetermined threshold, or not.

Figure 5:
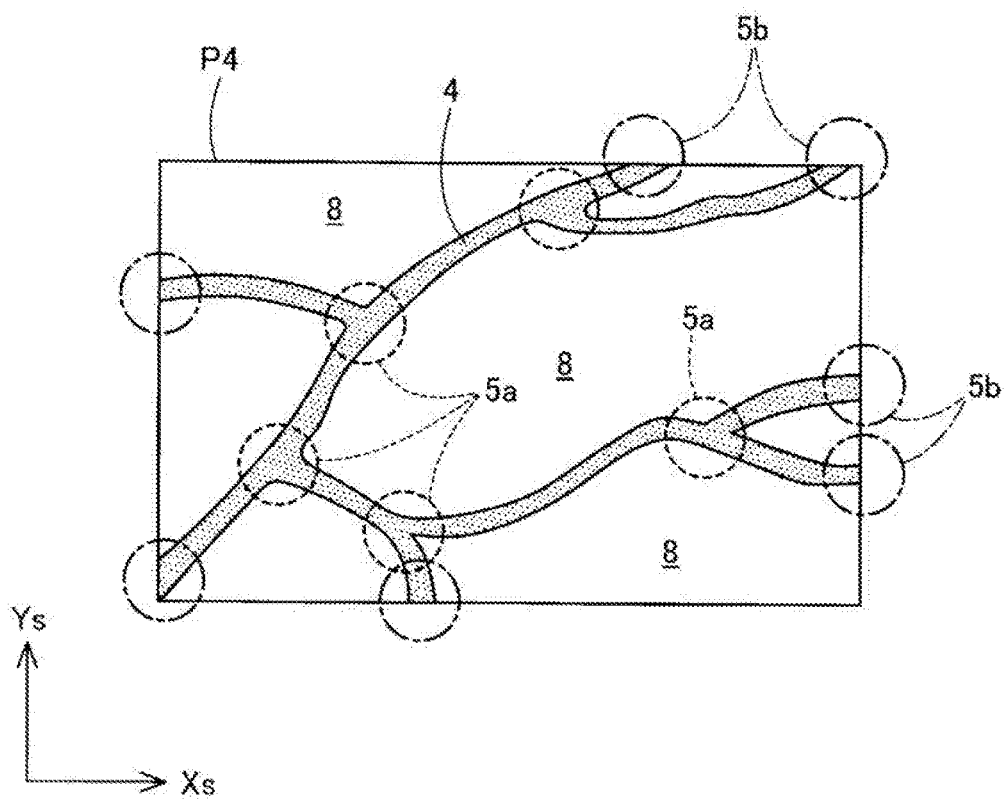
FIG. 5 shows an example of a blood vessel pattern acquired on the basis of a biological image.

FIG. 5 is a view showing an example of a blood vessel pattern P4 acquired on the basis of the biological image. The blood vessel pattern P4 is information indicating whether the blood vessel exists at each pixel forming the biological image, that is, the position of each light receiving element 59, corresponds to the blood vessel or the non-blood vessel area. In FIG. 5, the shaded strip-like part is a blood vessel 4, and the other solid white parts are extracted as non-blood vessel parts 8.

(A-2) Selection of Blood Vessel Site of Measurement Target

After the blood vessel pattern is acquired, a blood vessel to be measurement target (more specifically, a blood vessel site) is selected. The blood vessel site to be a measurement target is selected in such a way as to satisfy the following selection condition. The selection condition is that the blood vessel site should be "a site which is not a branching part or merging part of the blood vessel or the edges of the image and which has a predetermined length and predetermined width in the longitudinal direction of the blood vessel."

At a branching/merging part 5a (see FIG. 5) of the blood vessel, the light which has passed through a blood vessel that is not the measurement target can be mixed with the received light. The transmitted light through the blood vessel that is not the blood vessel site of the measurement target can affect the light absorption spectrum at the blood vessel site of the measurement target and thus can reduce measurement accuracy. Therefore, the blood vessel site of the measurement target is selected from blood vessel parts excluding the branching/merging part 5a of the blood vessel.

Also, at edges 5b (see FIG. 5) of the biological image, since structures such as branching and merging of the blood vessel near the outside of the image are unclear, there is a possibility of reduction in measurement accuracy for reasons similar to the above. To avoid this, the blood vessel site of the measurement target is selected from blood vessel parts excluding the edges 5b of the image.

The light cast from the light emitting elements 53 is diffused and reflected inside the living tissue, and a part of the light is received by the light receiving elements 59. That is, a part of the light received by the light receiving elements 59 becomes transmitted light through the target blood vessel, and the higher the proportion of the transmitted light is, the more significantly the characteristics of the blood components in the target blood vessel are expressed by the light absorption spectrum. That is, measurement accuracy becomes higher.

A blood vessel which appears relatively thin (blood vessel with a short length in the direction of width) is an inherently thin blood vessel and therefore a blood vessel located in a relatively deep position. The amount of light transmitted through such a blood vessel is small, causing a reduction in measurement accuracy. Therefore, the blood vessel site of the measurement target is selected from blood vessel parts excluding the blood vessel which appears thin (that is, from blood vessel sites having a predetermined width).

Figure 6:
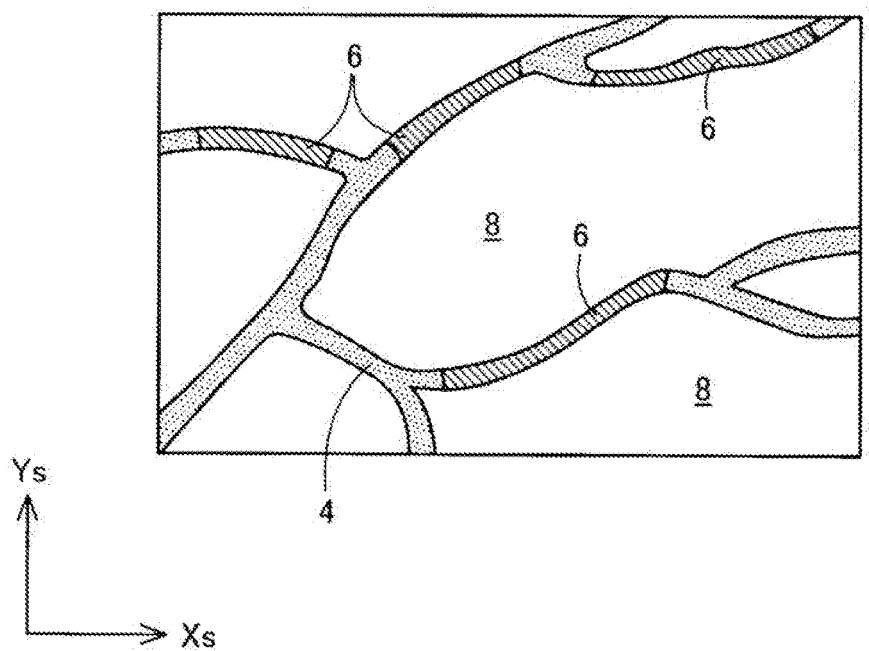
FIG. 6 shows an example of a blood vessel site which is a measurement target obtained on the basis of the blood vessel pattern of FIG. 5.

FIG. 6 shows an example of a blood vessel site 6 of a measurement target acquired on the basis of the blood vessel pattern P4 of FIG. 5. In FIG. 6, the parts hatched by slant lines, of the blood vessel 4, are the blood vessel sites 6 selected as measurement targets.

(A-3) Selection of Light Emitting Unit and Light Receiving Unit

Subsequently, a light emitting unit L and a light receiving unit S are selected.

Figure 7:
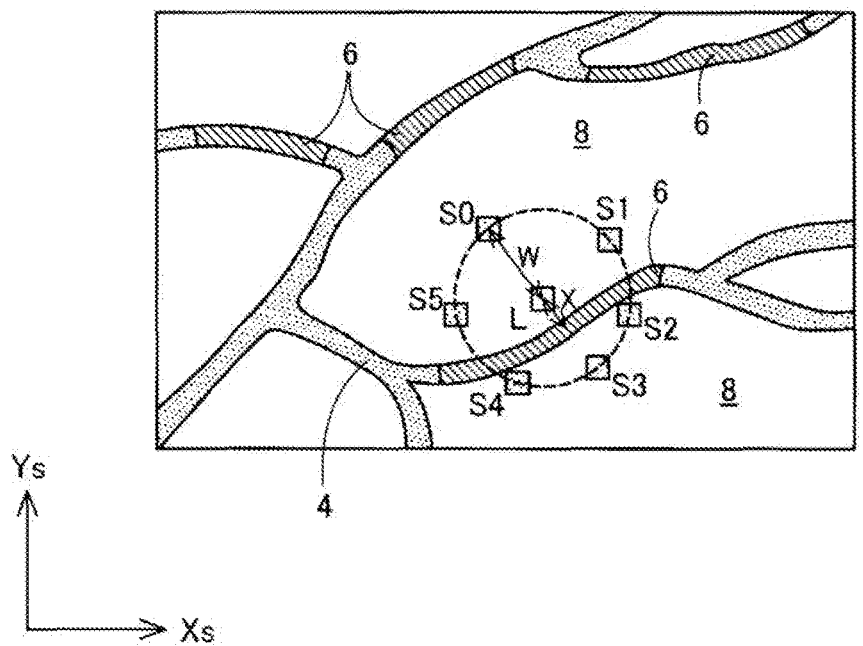
FIG. 7 illustrates the selection of a light emitting unit and a light receiving unit.

FIG. 7 illustrates the selection of a light emitting unit L and a light receiving unit S. In this embodiment, (i) a light emitting unit L spaced apart from the blood vessel by a distance X (second distance) is selected as a measurement light emitting unit Ld, and (ii) a plurality of light receiving units S spaced apart from the measurement light emitting unit Ld by a predetermined distance W (first distance), of a plurality of light receiving units S, is selected as measurement light receiving units Sd. Here, the "light emitting unit L spaced apart from the blood vessel by the distance X" means that the center of the light emitting unit L is spaced apart from the centerline of the blood vessel by the distance X±10%, and the "light receiving unit S spaced part from the measurement light emitting unit Ld by the first distance W" means that the center of the light receiving unit S is spaced apart from the center of the measurement light emitting unit Ld by the distance W±10%. Here, the centerline of the blood vessel refers to a line that is in the center in the direction of blood vessel width and along the direction of blood vessel length. In this embodiment, six measurement light receiving units S0, S1, S2, S3, S4, S5 are selected as the measurement light receiving units Sd. The predetermined distance W is defined as follows.

Figure 8:
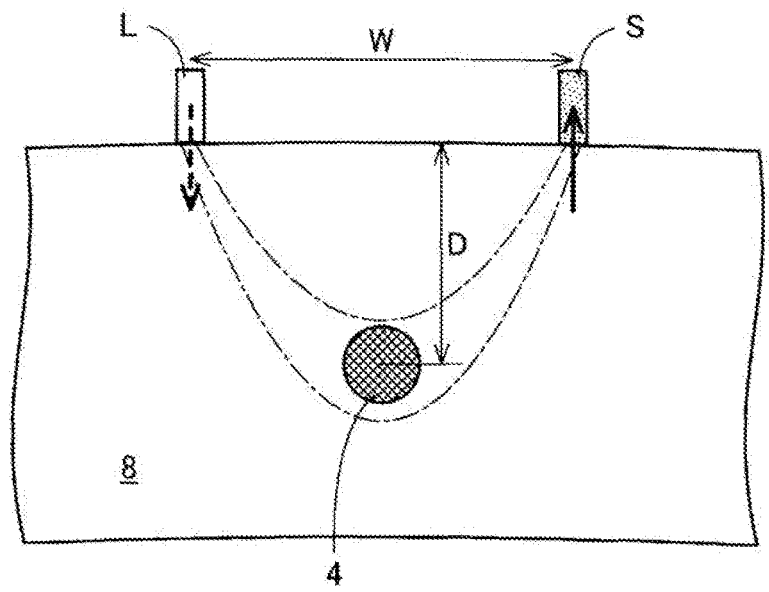
FIG. 8 illustrates the propagation of light within a living tissue.

FIG. 8 is a cross-sectional view taken along the direction of depth, illustrating the propagation of light within a living tissue. The light cast from a certain light emitting unit L is diffused and reflected within the living tissue and a part of the cast light reaches a certain light receiving unit S. The propagation path of the light is so-called banana-shaped (an area between two arcs). The propagation path has the broadest width in the direction of depth substantially near the middle, and its overall depth (depth that can be reached) becomes deeper according to the spacing between the light emitting elements 53 and the light receiving elements 59.

To increase measurement accuracy, it is desirable that a greater amount of transmitted light transmitted through the blood vessel 4 should be received by the light receiving unit S. Therefore, it is preferable that the target blood vessel 4 is located below the site between the light emitting unit L and the light receiving unit S, and the predetermined distance W corresponding to the presumed depth D of the target blood vessel 4 is determined. The predetermined distance W, that is, the optimum spacing W between the light emitting unit L and the light receiving unit S, is defined as approximately twice the depth D of the blood vessel 4 from the skin surface. For example, if the depth D is approximately 3 mm, the optimum distance W is approximately 5 to 6 mm.

The second distance X is preferably half the first distance W. In the case where the light emitting unit L at the position spaced apart from the blood vessel by half the first distance W is selected as the measurement light emitting unit Ld, if the target blood vessel 4 is present between the measurement light emitting unit Ld and the measurement light receiving unit Sd, a greater amount of the transmitted light transmitted through the target blood vessel 4 is received by the measurement light receiving unit Sd on the propagation path of the light emitted from the measurement light emitting unit Ld. Next, the relation between the light emitting unit L and the light emitting elements 53 and the relation between the light receiving unit S and the light receiving elements 59 will be described.

Figure 9:
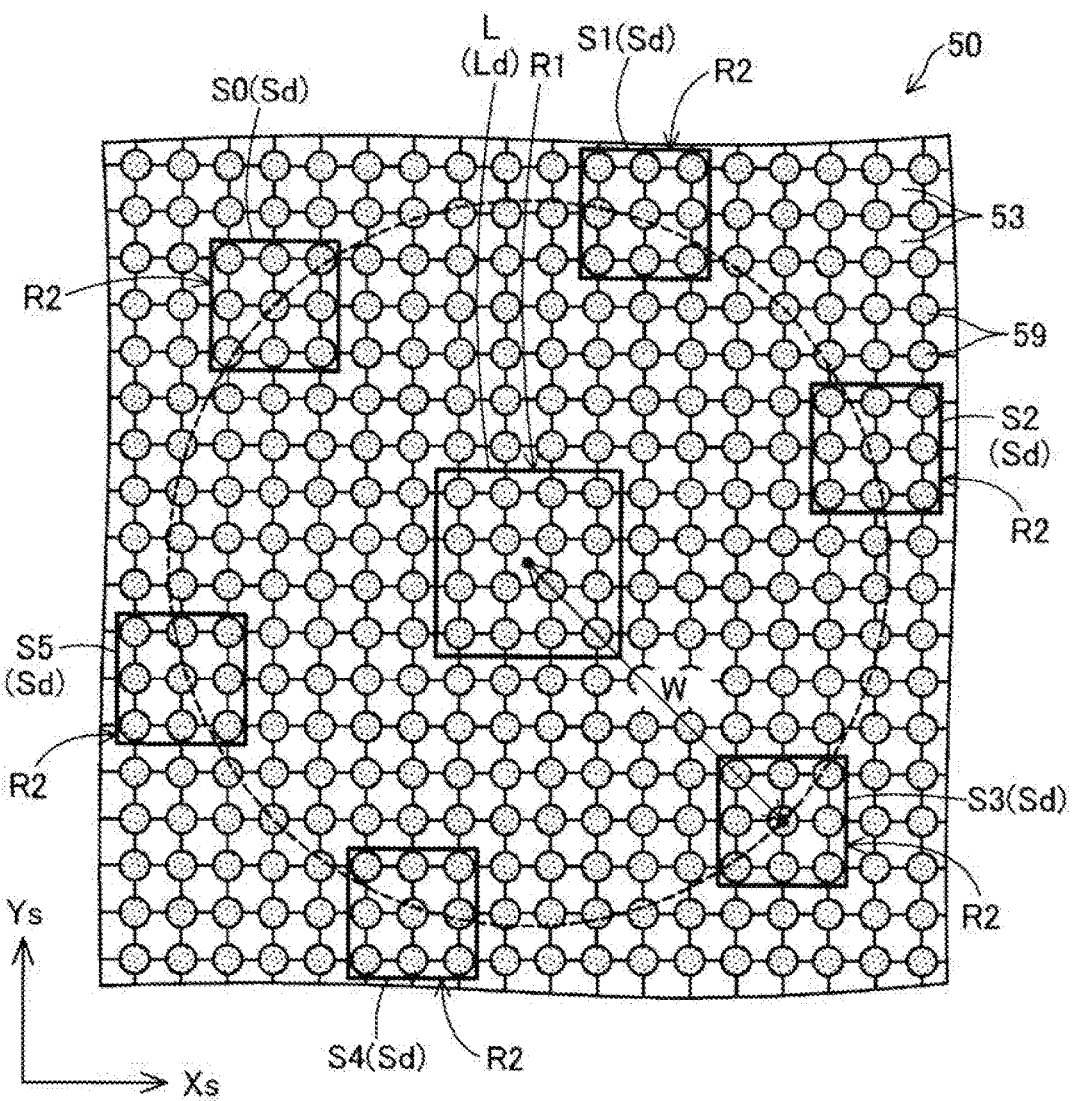
FIG. 9 shows the relation between a light emitting unit and light emitting elements and the relation between a light receiving unit and light receiving elements.

FIG. 9 shows the relation between the light emitting unit L and the light emitting elements 53 and the relation between the light receiving unit S and the light receiving elements 59. The light emitting unit L in this embodiment is made up of a plurality of light emitting elements 53 in a light emitting area R1. The light emitting area R1 refers to an area which is a part of the light emitting/receiving area of the sensor module 50 and which has a predetermined shape and size. In this embodiment, the light emitting area R1 is defined as an area containing three light emitting elements 53 vertically (in the Ys direction) by three light emitting elements 53 horizontally (in the Xs direction), and all of the light emitting elements 53 in the light emitting area R1 are made to emit light as the light emitting unit L. In this embodiment, the sensor module 50 has more than three light emitting elements 53 vertically (in the Ys direction) and more than three light emitting elements 53 horizontally (in the Xs direction). Therefore, a plurality of light emitting units L exists in the light emitting/receiving area of the sensor module 50. Then, a measurement light emitting unit Ld is selected from the plurality of light emitting units L. The area containing a plurality of light emitting elements 53 which is made to emit light as the measurement light emitting unit Ld is also referred to as a first light emitting area.

Also, the light emitting area having a predetermined shape and size may be an area corresponding to one light emitting element, for example. In this case, the one light emitting element 53 in this area is the light emitting unit L. It is also possible not to cause all the light emitting elements 53 in the light emitting area R1 to emit light.

Similarly, the light receiving unit S in this embodiment is made up of a plurality of light receiving elements 59 in a light receiving area R2. The light receiving area R2 refers to an area which is a part of the light emitting/receiving area of the sensor module 50 and which has a predetermined shape and size. In this embodiment, the light receiving area R2 is defined as an area containing three light receiving elements 59 vertically (in the Ys direction) by three light receiving elements 59 horizontally (in the Xs direction), and all of the light receiving elements 59 in the light receiving area R2 are made to receive light as the light receiving unit S. In this embodiment, the sensor module 50 has more than three light receiving elements 59 vertically (in the Ys direction) and more than three light receiving elements 59 horizontally (in the Xs direction). Therefore, a plurality of light receiving units S exists in the light emitting/receiving area of the sensor module 50. Then, a measurement light receiving unit Sd is selected from the plurality of light receiving units S. The area containing a plurality of light receiving elements 59 which is made to receive light as the measurement light receiving unit Sd is also referred to as a first light receiving area.

Also, the light receiving area R2 having a predetermined shape and size may be an area corresponding to one light receiving element 59, for example. In this case, the one light receiving element 59 in this light receiving area R2 is the light receiving unit S. It is also possible not to cause all the light receiving elements 59 in the light receiving area R2 to receive light. In this embodiment, the predetermined distance W between the light emitting unit L and the light receiving unit S is the distance between the centroid of the light emitting area R1 and the centroid of the light receiving area R2. These centroids are geometric centroids determined according to the shapes of the areas.

(A-4) Measurement

As the measurement light emitting unit Ld and the plurality of measurement light receiving units Sd with respect to the blood vessel site 6 of the measurement target are selected, measurement of the blood sugar level is carried out. Specifically, first, the measurement light emitting unit Ld is made to emit light and the plurality of measurement light receiving units Sd is made to receive the light, thus acquiring a plurality of light receiving results Q.

Next, of the plurality of light receiving results Q, a first light receiving result Q1 with the highest light reception intensity and a second light receiving result Q2 with the lowest light reception intensity are acquired. Then, a light absorption spectrum is generated using the first light receiving result Q1 and the second light receiving result Q2.

Figure 10:
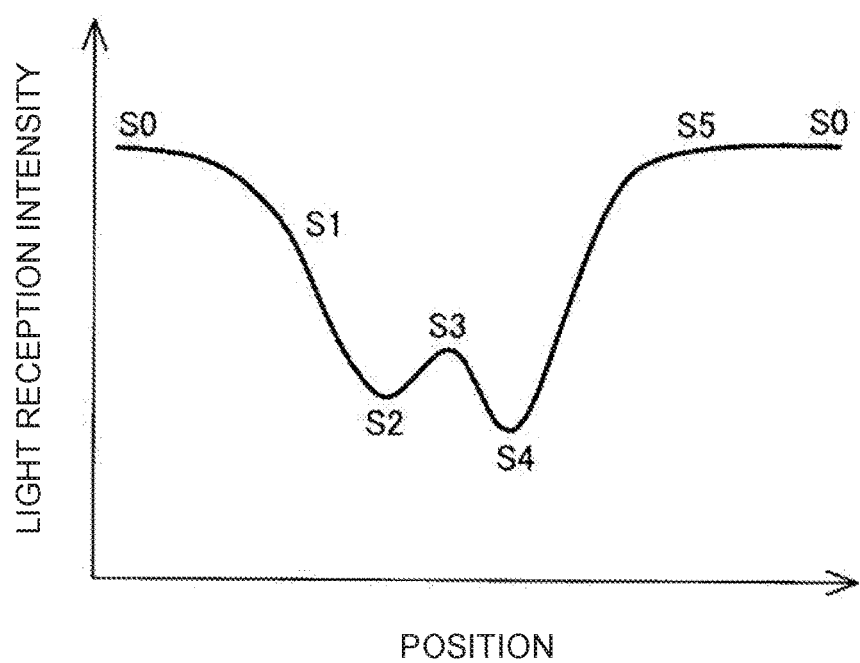
FIG. 10 shows the light reception intensity acquired by a plurality of measurement light receiving units Sd.

FIG. 10 shows the light reception intensity acquired by the plurality of measurement light receiving units Sd. The vertical axis in FIG. 10 represents the light reception intensity. The horizontal axis in FIG. 10 represents the positions of the plurality of measurement light receiving units Sd, which are positions in the circumferential direction about the light emitting unit L and moving clockwise, starting from the measurement light receiving unit 50. The positions of the measurement light receiving units Sd in FIG. 10 correspond to the positions of the measurement light receiving units Sd in FIG. 9. In this embodiment, as shown in FIG. 10, the measurement light receiving unit S0 has the highest light reception intensity and the measurement light receiving unit S4 has the lowest light reception intensity. Therefore, the light receiving result of the measurement light receiving unit S0 is the first light receiving result Q1 and the light receiving result of the measurement light receiving unit S4 is the second light receiving result Q2.

Here, the light reception intensity means the integral value of the transmittance obtained by changing the wavelength of the cast light from 720 nm to 800 nm. The transmittance TOO is obtained as $T(\lambda)=Os(\lambda)/Or(\lambda)$ based on the light intensity $Os(\lambda)$ obtained by the measurement light receiving unit S4 and the light intensity $Or(\lambda)$ obtained by the measurement light receiving unit S0. Then, the light absorptivity is found from the transmittance, and the light absorption spectrum is generated.

Here, the computational principle for transmittance will be briefly described. Generally, if the intensity of the light cast from the light emitting unit L is $P(\lambda)$, the transmittance of an object part through which the cast light is transmitted is $T(\lambda)$, and the sensitivity determined for the light receiving unit S is $S(\lambda)$, the light intensity $O(\lambda)$ obtained by the light receiving unit S is given as $O(\lambda)=P(\lambda)\times T(\lambda)\times S(\lambda)$.

Based on this relational expression, the light intensity $Or(\lambda)$ obtained by the measurement light receiving unit S0, not including the transmitted light through the blood vessel 4, is $Or(\lambda)=P(\lambda)\times S(\lambda)$ if the transmittance $T(\lambda)$ of the non-blood vessel part is "1".

Meanwhile, the light intensity $Os(\lambda)$ obtained by the measurement light receiving unit S4, including the transmitted light through the blood vessel 4, is $Os(\lambda)=P(\lambda)\times T(\lambda)\times S(\lambda)$. The transmittance $T(\lambda)$ is found from these two formulae. Also, the transmittance $T(\lambda)$ is a relative value to the transmittance of the non-blood vessel part 8.

(A-5) Calculation of Blood Sugar Level

Subsequently, based on the light absorption spectrum, the blood sugar level is estimated and calculated, using a calibration curve expressing a predetermined relation between blood sugar level (blood glucose concentration) and light absorptivity. The technique for calculating the concentration of a predetermined component (in this embodiment, glucose) from the light absorption spectrum is already known. In this embodiment, this known technique can be applied.

A3. Functional Configuration

Figure 11:
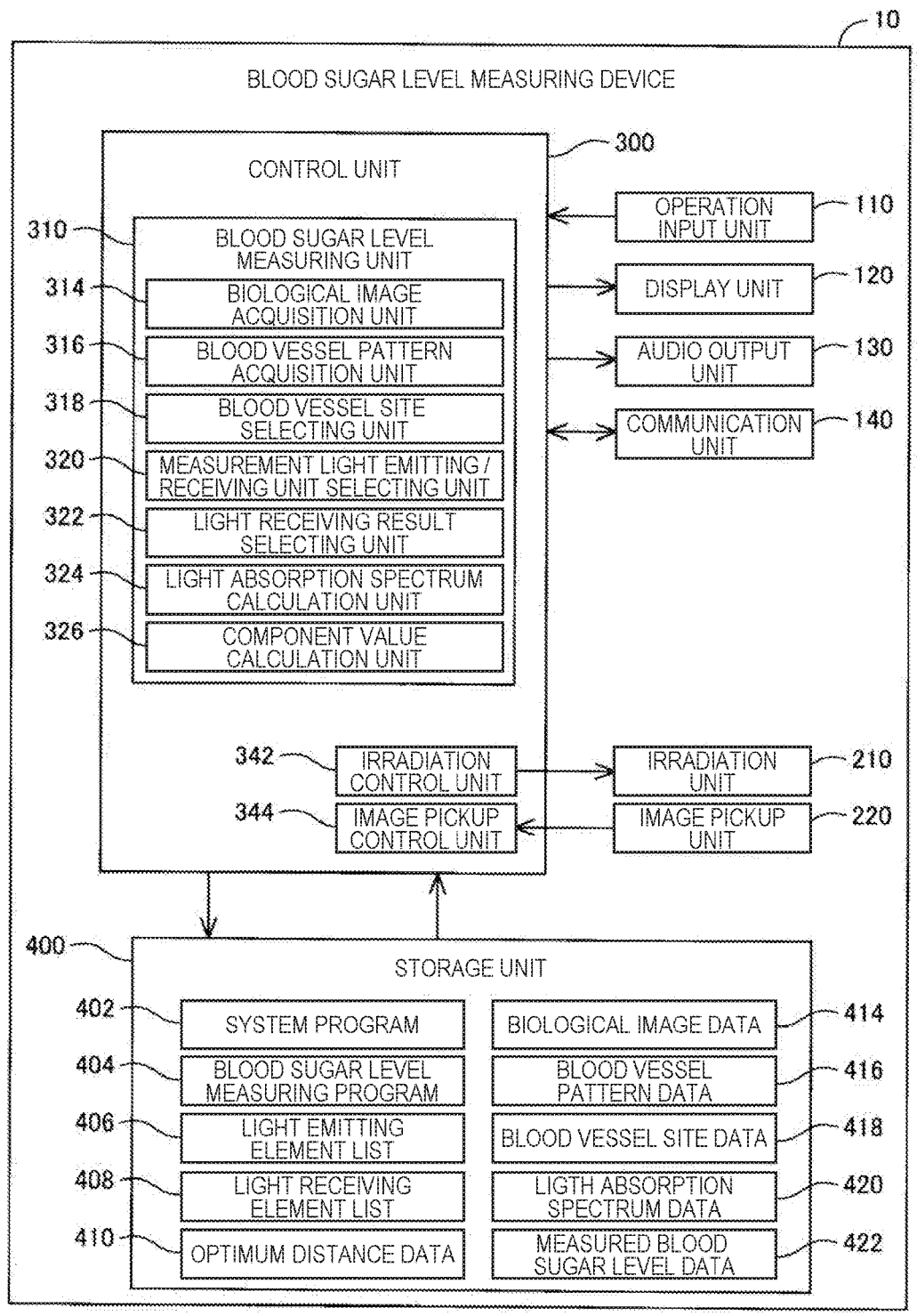
FIG. 11 shows the functional configuration of a blood sugar level measuring device according to the embodiment.

FIG. 11 shows the functional configuration of the blood sugar level measuring device 10 in this embodiment. In terms of its functions, the blood sugar level measuring device 10 has an operation input unit 110, a display unit 120, an audio output unit 130, a communication unit 140, an irradiation unit 210, an image pickup unit 220, a control unit 300, and a storage unit 400.

The operation input unit 110 is an input device such as a button switch, touch panel and various sensors, and outputs an operation signal corresponding to an operation that is carried out, to the control unit 300. With the operation input unit 110, various instructions such as a blood sugar level measurement start instruction are inputted. In FIG. 1, the operation switch 18 and the touch panel 16 are equivalent to this.

The display unit 120 is a display device such as an LCD (liquid crystal display) and carries out various displays based on display signals from the control unit 300. The result of measurement or the like is displayed on the display unit 120. In FIG. 1, the touch panel 16 is equivalent to this.

The audio output unit 130 is an audio output device such as a speaker and outputs various sounds based on audio signals from the control unit 300. By the audio output unit 130, a notification sound for the start or end of measurement of the blood sugar level, or the occurrence of low blood sugar level is output.

The communication unit 140 is a communication device such as a wireless communication machine and a modem, or a communication cable outlet and a control circuit for wired communication. The communication unit 140 is connected to a communication network and realizes communication with the outside. In FIG. 1, the communication device 20 is equivalent to this.

The irradiation unit 210 has multiple light emitting elements 53 which are two-dimensionally arrayed on a plane. The light emitting layer 52 of the sensor module 50 shown in FIG. 2 is equivalent to this. The arrangement position of the irradiation unit 210 (specifically, the position coordinates of each light emitting element 53 in the Xs-Ys orthogonal coordinate system) is stored as a light emitting element list 406.

The image pickup unit 220 has multiple light receiving elements 59 which are two-dimensionally arrayed on a plane. The light receiving layer 58 of the sensor module 50 shown in FIG. 2 is equivalent to this. The arrangement position of the image pickup unit 220 (specifically, the position coordinates of each light receiving element 59 in the Xs-Ys orthogonal coordinate system) is stored as a light receiving element list 408.

The control unit 300 is realized, for example, by a microprocessor such as CPU or GPU (graphics processing unit), and electronic components such as an ASIC (application specific integrated circuit) and IC memory. The control unit 300 executes various kinds of computational processing based on predetermined program, data or an operation signal from the operation input unit 110 and controls the operation of the blood sugar level measuring device 10. In FIG. 1, the control board 30 is equivalent to this. Also, the control unit 300 has a blood sugar level measuring unit 310, an irradiation control unit 342, and an image pickup control unit 344. The irradiation control unit 342 selectively controls the light emission of each of the plurality of light emitting elements 53. The image pickup control unit 344 acquires the amount of light received by each of the plurality of light receiving elements 59.

The blood sugar level measuring unit 310 has a biological image acquisition unit 314, a blood vessel pattern acquisition unit 316, a blood vessel site selecting unit 318, a measurement light emitting/receiving unit selecting unit 320, a light receiving result selecting unit 322, a light absorption spectrum calculation unit 324, and a component value calculation unit 326, and measures the blood glucose concentration, that is, blood sugar level, of the user 2.

The biological image acquisition unit 314 acquires a biological image of the user 2. The acquisition of the biological image is realized by suitably using a biological image pickup technique in a known vein authentication technique or the like. That is, the light emitting elements 53 are made to emit light at a time and photometry (image pickup) by all of the light receiving elements 59 is carried out. Then, a luminance image based on the result of the photometry, that is, a biological image, is generated. The biological image acquired by the biological image acquisition unit 314 is stored as biological image data 414.

The blood vessel pattern acquisition unit 316 carries out predetermined image processing on the biological image acquired by the biological image acquisition unit 314 and thus acquires a blood vessel pattern. Specifically, the acquisition of the blood vessel pattern is realized by suitably using a technique for identifying a vein pattern from a biological image in a known vein authentication technique. For example, on each pixel of the biological image, the luminance is compared with reference luminance and binarization or filter processing is performed. Pixels with luminance below the reference luminance represent a blood vessel, and pixels with luminance equal to or above the reference luminance represent a non-blood vessel area. The blood vessel pattern acquired by the blood vessel pattern acquisition unit 316 is stored as blood vessel pattern data 416.

The blood vessel site selecting unit 318 selects a blood vessel site 6 indicating a predetermined selection condition, as a measurement target, on the basis of the blood vessel pattern acquired by the blood vessel pattern acquisition unit 316. Here, there may be one or a plurality of blood vessel sites 6 to be a measurement target. Each of the blood vessel sites 6 selected as a measurement target is stored as blood vessel site data 418.

Figure 12:
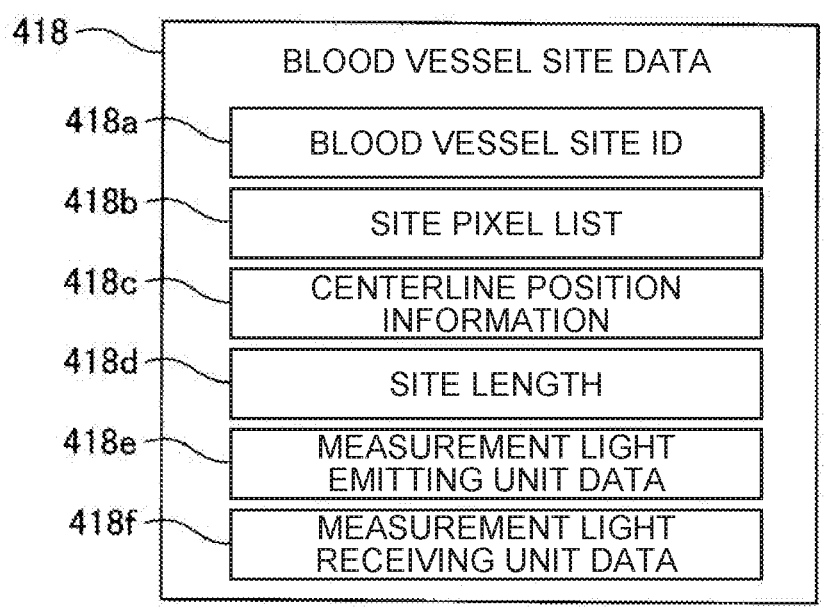
FIG. 12 shows an example of the data configuration of blood vessel site data.

FIG. 12 shows an example of the data configuration of the blood vessel site data 418. The blood vessel site data 418 stores blood vessel site ID 418a which is the identification information of this blood vessel site, site pixel list 418b, centerline position information 418c, site length 418d which is the length in the longitudinal direction of the blood vessel, measurement light emitting unit data 418e, and measurement light receiving unit data 418f. The site pixel list 418b is a list of pixels (that is, light receiving elements 59) corresponding to this blood vessel site. The centerline position information 418c is the information of the position coordinates of the centerline of this blood vessel site (a line in the center in the direction of blood vessel width and along the direction of blood vessel length) in the Xs-Ys orthogonal coordinate system.

The measurement light emitting/receiving unit selecting unit 320 selects a measurement light emitting unit Ld and a measurement light receiving unit Sd for each of the blood vessel sites 6 of the measurement target. Specifically, in the Xs-Ys orthogonal coordinate system (that is, on the skin surface), one position spaced apart from the blood vessel site 6 by a second distance X is selected as the measurement light emitting unit Ld, and a measurement light receiving unit Sd spaced apart from the measurement light emitting unit Ld by a predetermined distance W is selected. The predetermined distance W is stored as optimum distance data 410. As a method for selecting the one position spaced apart from the blood vessel site 6 by the second distance X, for example, a position spaced apart from the blood vessel site 6 by the second distance X is defined as this position. The selected measurement light emitting unit Ld is stored as the measurement light emitting unit data 418e. The selected measurement light receiving unit Sd is stored as the measurement light receiving unit data 418f.

The light receiving result selecting unit 322 selects a first light receiving result Q1 with the highest light reception intensity and a second light receiving result Q2 with the lowest light reception intensity, from among the plurality of light receiving results Q obtained from the plurality of measurement light receiving units Sd.

The light absorption spectrum calculation unit 324 generates a light absorption spectrum for each of the blood vessel sites 6 of the measurement target. Specifically, the light absorption spectrum is generated by calculating the transmittance T for each wavelength λ on the basis of the first light receiving result Q1 and the second light receiving result Q2. Moreover, if there is a plurality of blood vessel sites 6 of the measurement target, the light absorption spectra of the plurality of blood vessel sites 6 of the measurement target is averaged, thus calculating an average light absorption spectrum. The light absorption spectrum calculated by the light absorption spectrum calculation unit 324 is stored as light absorption spectrum data 420.

The component value calculation unit 326 calculates the glucose concentration (that is, blood sugar level), which is a target concentration of a blood component in the blood, on the basis of the light absorption spectrum calculated by the light absorption spectrum calculation unit 324. In this embodiment, an analysis method such as multiple regression analysis, principal component regression analysis, PLS regression analysis, or independent component analysis is used on the light absorption spectrum. If there is a plurality of blood vessel sites 6 of the measurement target, the blood sugar level is calculated from the average light absorption spectrum obtained by averaging the light absorption spectrum about the respective blood vessel sites 6. The blood sugar level calculated by the component value calculation unit 326 is accumulated and stored as measured blood sugar level data 422, associated with the time of measurement.

The storage unit 400 is a storage device such as a ROM, RAM or hard disk. The storage unit 400 stores programs and data or the like for the control unit 300 to integrally control the blood sugar level measuring device 10, and is also used as a work area for the control unit 300, where the result of computations executed by the control unit 300 and operation data or the like from the operation input unit 110 are temporarily stored. In FIG. 1, the main memory and the measurement data memory installed on the control board 30 are equivalent to this. Also, in the storage unit 400, a system program 402, a blood sugar level measuring program 404, the light emitting element list 406, the light receiving element list 408, the optimum distance data 410, the biological image data 414, the blood vessel pattern data 416, the blood vessel site data 418, the light absorption spectrum data 420, and the measured blood sugar level data 422 are stored.

A4. Biological Information Acquisition Method

Figure 13:
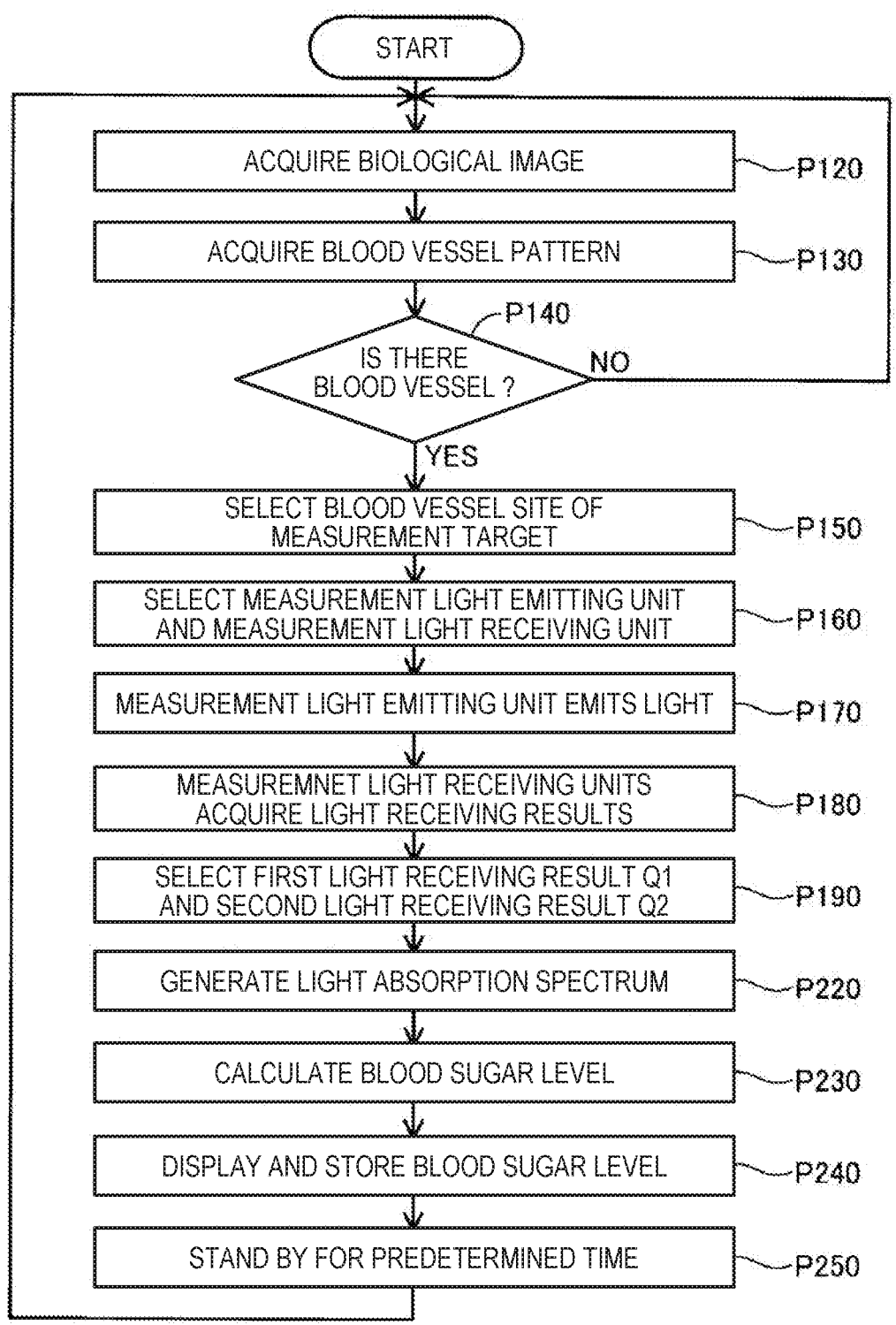
FIG. 13 is a flowchart for explaining the flow of blood sugar level measuring processing.

FIG. 13 is a flowchart illustrating the flow of blood sugar level measuring processing as a biological information acquisition method. This processing is realized by the control unit 300 executing processing according to the blood sugar level measuring program 404.

According to FIG. 13, the blood sugar level measuring unit 310 carries out measuring processing in which the blood sugar level of the user is measured. First, the biological image acquisition unit 314 of the blood sugar level measuring unit 310 sets the entire light emitting surface of the sensor module 50 (that is, the range including all of the light emitting elements 53) as a light emitting range, and causes the light emitting elements 53 within the light emitting range to emit light, thus acquiring a biological image of the user (Step P120). Next, the blood vessel pattern acquisition unit 316 acquires a blood vessel pattern as viewed from the skin surface, on the basis of the acquired biological image (Step P130). If no blood vessel pattern is acquired as a result (Step P140, NO), the processing returns to step P120.

If a blood vessel pattern is acquired (Step P140, YES), the blood vessel site selecting unit 318 selects a blood vessel site 6 of a measurement target that satisfies a predetermined selection condition on the basis of the acquired blood vessel pattern (Step P150). Then, the measurement light emitting/receiving unit selecting unit 320 selects a measurement light emitting unit Ld and a plurality of measurement light receiving units Sd (Step P160). Next, the measurement light emitting unit Ld is made to emit light (Step P170), and a plurality of light receiving results Q is acquired by the plurality of measurement light receiving units Sd (Step P180).

After that, the light receiving result selecting unit 322 selects a first light receiving result Q1 with the highest light reception intensity and a second light receiving result Q2 with the lowest light reception intensity, of the plurality of light receiving results Q (Step P190). Next, the light absorption spectrum calculation unit 324 generates a light absorption spectrum for this blood vessel site 6, using the first light receiving result Q1 and the second light receiving result Q2 (Step P220). Also, if there is a plurality of blood vessel sites 6 of the measurement target, the average of the light absorption spectra of the respective blood vessel sites 6 is calculated.

After that, the component value calculation unit 326 calculates the blood glucose concentration, that is, blood sugar level, on the basis of the light absorption spectrum (Step P230). Then, the calculated blood sugar level is displayed on the display unit 120 and is accumulated and stored in association with the time of measurement (Step P240). After the lapse of a predetermined standby time (Step P250), the processing returns to Step P120 and the next blood sugar level is similarly measured.

A5. Advantageous Effects

As described above, since a blood vessel absorbs near-infrared rays more easily than non-blood vessel parts, the luminance of the light transmitted through the blood vessel is lower than the luminance of the light that is not transmitted through the blood vessel. Also, capillaries are present everywhere in the human body. The biological information acquisition device 10 of the embodiment acquires biological information, using (i) the first light receiving result Q1, which is the light receiving result with the highest light reception intensity and is considered to include little biological information related to the blood vessel, and (ii) the second light receiving result Q2, which is the light receiving result with the lowest light reception intensity and is considered to include a lot of biological information related to the blood vessel. Therefore, the biological information acquisition device 10 can acquire biological information with high accuracy.

Also, in the biological information acquisition device 10 of the embodiment, after the position of the blood vessel site 6 in the living body is specified, the light emitting unit L spaced apart from the blood vessel site 6 by the second distance X, of the plurality of light emitting units, is selected as the measurement light emitting unit Ld. Since the position of the blood vessel is thus specified in advance and the measurement light emitting unit Ld is selected on the basis of the position of the blood vessel, the light emitting unit L suitable for acquiring biological information related to the blood vessel can be selected as the measurement light emitting unit Ld. Therefore, the biological information related to the blood vessel can be acquired with high accuracy.

In the biological information acquisition device 10 of the embodiment, the control unit 300 selects the light emitting area R1 having a predetermined shape and size as a part of the light emitting/receiving area, and causes a plurality of light emitting elements 53 in the selected light emitting area R1 to emit light as the measurement light emitting unit Ld. In this way, the light emitting unit L in the embodiment is made up of a plurality of light emitting elements 53. Therefore, compared with the case where one light emitting unit is made up of one light emitting element, the biological information acquisition device 10 of the embodiment can achieve sufficient light emission intensity. Consequently, the biological information acquisition device 10 of the embodiment can acquire the biological information with high accuracy.

Similarly, in the biological information acquisition device 10 of the embodiment, the control unit 300 selects the light receiving area R2 having a predetermined shape and size as a part of the light emitting/receiving area, and causes a plurality of light receiving elements 59 in the selected light receiving area R2 to receive light as the measurement light receiving unit Sd. In this way, the light receiving unit S in the embodiment is made up of a plurality of light receiving elements 59. Therefore, compared with the case where one light receiving unit is made up of one light receiving element, the biological information acquisition device 10 of the embodiment can achieve a sufficient amount of light received. Consequently, the biological information acquisition device 10 of the embodiment can acquire the biological information with high accuracy.

In the biological information acquisition device 10 of the embodiment, since one light emitting unit L is made up of a set of a plurality of smaller light emitting elements 53, the position of the light emitting unit L can be selected on the basis of the pitch of the smaller light emitting elements 53. Therefore, according to the biological information acquisition device 10 of the embodiment, the degree of freedom in selecting the light emitting unit L is improved.

Similarly, in the biological information acquisition device 10 of the embodiment, since one light receiving unit S is made up of a set of a plurality of smaller light receiving elements 59, the position of the light receiving unit S can be selected on the basis of the pitch of the smaller light receiving elements 59. Therefore, according to the biological information acquisition device 10 of the embodiment, the degree of freedom in selecting the light receiving unit S is improved.

B. Modifications

The invention is not limited to the embodiment examples and their modifications and can be carried out in various other forms without departing from the scope of the invention. For example, the following modifications are possible.

B1. Modification 1

In the biological information acquisition device of the embodiment, the control unit 300 may select a plurality of measurement light receiving units Sd in such a way that the light receiving areas R2 of adjacent measurement light receiving units Sd partly overlap with each other. Thus, the position of each of the plurality of measurement light receiving units can be selected on the basis of the pitch of the light receiving elements and therefore the degree of freedom in selecting the light receiving unit is improved. Consequently, according to the biological information acquisition device of the embodiment with this configuration, the biological information related to the blood vessel can be acquired with high accuracy.

B2. Modification 2

In the embodiment, the light receiving unit S spaced apart from the light emitting unit L by the predetermined distance W is selected after the selection of the light emitting unit L. However, the invention is not limited to this. The light emitting unit L spaced apart from the light receiving unit S by the predetermined distance W may be selected after the selection of the light receiving unit S.

B3. Modification 3

In the embodiment, the blood sugar level is acquired as biological information. However, the invention is not limited to this. For example, the oxygen saturation level in the blood of the user as a living body may be acquired as the biological information. The oxygen saturation level in the blood refers to the proportion of the hemoglobin coupled to oxygen, of the hemoglobin in red blood cells. The hemoglobin in the blood has different degrees of absorption of red light and infrared rays, depending on whether the hemoglobin is coupled to oxygen or not. Thus, the oxygen saturation level can be acquired, for example, by using a plurality of sets of elements with different light emission wavelength and light reception wavelengths, such as elements which emit or receive red light or elements which emit or receive infrared rays.

B4. Modification 4

In the embodiment, the light emission by the light emitting unit L is carried out (Step P170), after the selection of the light emitting unit L and the light receiving unit S (Step P160). However, the invention is not limited to this. The selection of the light receiving unit S may be carried out after the light emission by the light emitting unit L.

B5. Modification 5

In the embodiment, a plurality of light emitting units L is provided and the measurement light emitting unit Ld is selected according to the position of the blood vessel. However, the invention is not limited to this. There may be only one light emitting unit L. Also, a light emitting unit may be provided in a predetermined position regardless of the position of the blood vessel.

B6. Modification 6

In the embodiment, the first light receiving result Q1 with the highest light reception intensity and the second light receiving result Q2 with the lowest light reception intensity are selected. However, the invention is not limited to this. A light receiving result with the fifth highest light reception intensity or so may be selected as the first light receiving result Q1, and a light receiving result with the fifth lowest light reception intensity may be selected as the second light receiving result Q2. By avoiding the light receiving result with the highest light reception intensity and the light receiving result with the lowest light reception intensity, it is possible to avoid selecting noise data.

Of the component elements in the embodiment examples and modifications, the elements other than those described in the independent claims are supplementary elements and therefore can be omitted according to need.

The entire disclosure of Japanese Patent Application No. 2016-018549 filed on Feb. 3, 2016 is hereby incorporated herein by reference.

What is claimed is:

1. A biological information acquisition device comprising:
    a light source configured to emit light on a living body;
    a plurality of imaging sensors configured to receive passing light that is obtained by transmitting the light through the living body, each of the plurality of imaging sensors being spaced apart from the light source by the same distance;
    a memory configured to store computer-readable instructions; and
    processor configured to execute the computer-readable instructions so as to control the light source and the plurality of imaging sensors,
    wherein the processor is further configured to:
        cause each of the plurality of imaging sensors to receive the passing light;
        determine intensities of the passing lights received by the plurality of the imaging sensors;
        determine a highest intensity and a lowest intensity among the intensities;
        determine a highest intensity reception sensor that received the passing light with the highest intensity and a lowest intensity reception sensor that received the passing light with the lowest intensity among the plurality of imaging sensors; and
        acquire biological information based on degrees of the highest and lowest intensities and locations of the highest and lowest intensity reception sensors.

2. The biological information acquisition device according to claim 1, comprising
    a plurality of the light sources,
    wherein the processor is configured to:
        locate the position of a blood vessel in the living body by causing at least one of the plurality of light sources to emit the light, and
        select only one of the plurality of light sources that is spaced apart from the blood vessel by a second distance to emit the light toward the living body.

3. The biological information acquisition device according to claim 1, comprising
    a sensor module having a plurality of the light sources and the plurality of imaging sensors, each being arrayed regularly, in an area from which the light is emitted and by which the passing light is received,
    wherein the processor is configured to select a light emitting area having a predetermined shape and size within the area, and
    the processor is configured to cause the plurality of the light sources located in the light emitting area to emit the light onto the living body.

4. The biological information acquisition device according to claim 1, comprising
    a sensor module having a plurality of the light sources and the plurality of imaging sensors, each being arrayed regularly, in an area from which the light is emitted and by which the passing light is received,
    wherein the processor is configured to select a light receiving area having a predetermined shape and size within the area, and
    the processor is configured to cause the plurality of imaging sensors located in the light receiving area to receive the passing light from the living body.

5. The biological information acquisition device according to claim 4, wherein
    each of the plurality of imaging sensors has a light receiving area corresponding to an area of the living body from which the passing light is generated, and
    the light receiving areas of the plurality of imaging sensors located in the light receiving area overlap with each other.

6. The biological information acquisition device according to claim 1, wherein
    the biological information includes glucose concentration in blood in a blood vessel of the living body.

7. The biological information acquisition device according to claim 1, wherein
    the biological information includes oxygen saturation level in blood in a blood vessel of the living body.

8. A biological information acquisition method for causing a processor to execute computer-readable instructions stored in a memory, the method comprising executing on the processor the steps of:
    causing a light source to emit light on a living body;
    causing each of a plurality of imaging sensors to receive passing light that is obtained by transmitting the light through the living body, each of the plurality of imaging sensors being spaced apart from the light source by the same distance;
    determining intensities of the passing lights received by the plurality of the imaging sensors;
    determining a highest intensity and a lowest intensity among the intensities;
    determining a highest intensity reception sensor that received the passing light with the highest intensity and a lowest intensity reception sensor that received the passing light with the lowest intensity among the plurality of imaging sensors; and
    acquiring biological information based on degrees of the highest and lowest intensities and locations of the highest and lowest intensity reception sensors.

* * * * *